United States Patent [19]

Latorse

[11] Patent Number: 5,556,880
[45] Date of Patent: Sep. 17, 1996

[54] FUNGICIDAL COMBINATIONS BASED ON A PHENYLBENZAMIDE

[75] Inventor: Marie-Pascale Latorse, Sourcieux Les Mines, France

[73] Assignee: Rhone-Poulenc Agrocimie, Lyon Cedex, France

[21] Appl. No.: 322,504

[22] Filed: Oct. 14, 1994

[30] Foreign Application Priority Data

Oct. 14, 1993 [FR] France ................................ 93 12465

[51] Int. Cl.$^6$ ............................ A01N 37/18; A01N 47/10
[52] U.S. Cl. ......................... 514/491; 514/476; 514/622
[58] Field of Search .................................. 514/476, 491, 514/622

[56] References Cited

U.S. PATENT DOCUMENTS 4,886,825  12/1989  Ruess et al. ............................. 514/383
5,342,835   8/1994  Pepin et al. ........................... 514/227.5

FOREIGN PATENT DOCUMENTS 0360701  3/1990  European Pat. Off. .
0578586  1/1994  European Pat. Off. .

OTHER PUBLICATIONS

Warthing et al, The Pesticide Manual, 9th Ed. (1991) pp. 531–532.

*Primary Examiner*—Allen J. Robinson
*Attorney, Agent, or Firm*—Burns, Doane, Swecker & Mathis, L.L.P.

[57] ABSTRACT

The invention provides fungicidal combinations comprising:
(a) a compound of formula A

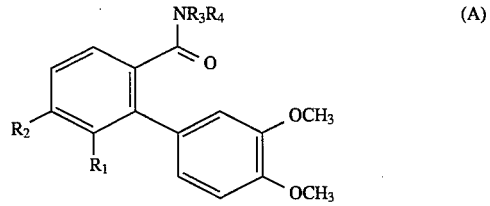

wherein each of $R_1$ and $R_2$, which are identical or different, is H, Hal or optionally halogenated lower alkyl, and each of $R_3$ and $R_4$, which are identical or different, is ($C_1$–$C_4$) alkyl, and
(b) at least one compound B selected from the group consisting of maneb, mancozeb, folpet, a copper derivative, phosethyl-Al or phosphorous acid or one of its alkali metal or alkaline-earth metal salts, chlorothalonil, fluazinam, an acylalanine, an acetamide, a methoxyacrylate or a methoxyiminoacetate.

Fungicidal compositions comprising the combination and methods for curatively and preventatively treating plants against fungal disease are also provided.

16 Claims, 7 Drawing Sheets

FUNGICIDAL COMBINATIONS BASED ON A PHENYLBENZAMIDE

FIELD OF THE INVENTION

The subject of the present invention is a fungicidal combination based on a derivative of phenylbenzamide type, its preparation and its use in protecting plants against fungal diseases.

BACKGROUND OF THE INVENTION

EP 0360701 (corresponding to Pepin et al U.S. Pat. No. 5,342,835) describes a very large number of amide derivatives and especially phenylbenzamides, as well as their use as active materials for controlling fungal diseases. The examples show, in particular, preventive activity against diseases such as blights and mildews.

In accord with the present invention, it has now been discovered that a combination of a narrow selection of these phenylbenzamide derivatives with other specific fungicities exhibits remarkable and surprising synergistic properties which open new applicational possibilities.

SUMMARY OF THE INVENTION

More precisely, the present invention relates to a fungicidal combination comprising:

(a) a compound of the formula A

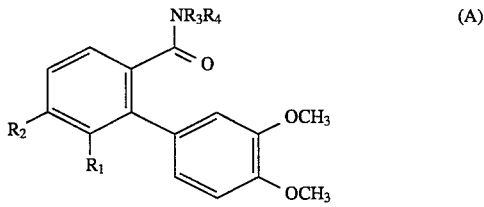

wherein each of $R_1$ and $R_2$, which are identical or different, is a hydrogen or halogen atom or an optionally halogenated lower alkyl radical, and each of $R_3$ and $R_4$, which are identical or different, is an alkyl radical having 1 to 4 carbon atoms; and (b) at least one Compound B selected from the group consisting of: maneb [manganese ethylenebis(dithiocarbamate)]; mancozeb [zinc and manganese ethylenebis(dithiocarbamate)]; folpet (trichloromethyl-thioisoindolinedione); a copper derivative; phosethyl-Al [aluminum tris(O-ethylphosphonate)], or phosphorous acid or one of its alkali metal or alkaline-earth metal salts; chlorothalonil (tetrachloroisophthalonitrile); fluazinam [N-(3-chloro-5-trifluoromethyl-2-pyridyl)-2,6-dinitro-3-chloro-4-(trifluoromethyl)aniline]; an acylalanine; an acetamide; a methoxyacrylate; and a methoxyiminoacetate.

DESCRIPTION OF THE DRAWINGS

The objects and advantages of the present invention will be apparent from the following detailed description and accompanying drawings in which.

Figure 1:
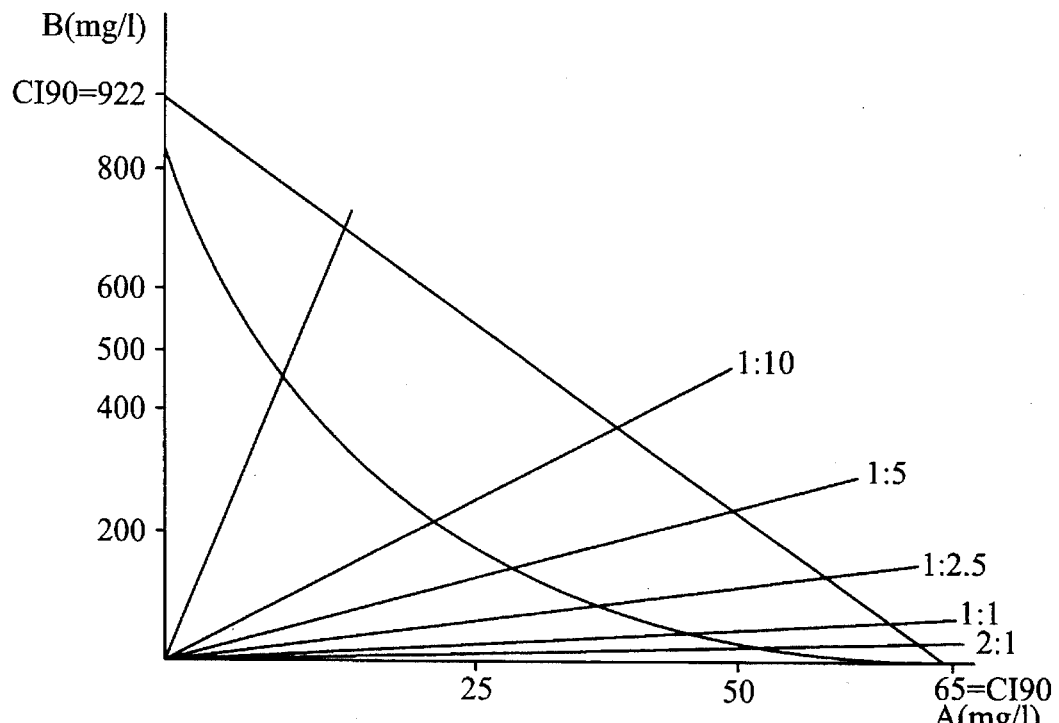
FIG. 1 is a Tammes isobole diagram based on tests of vine cuttings infected with *Plasmopara viticola* before or after treatment with N-methyl-N-ethyl-2-(3,4-dimethoxyphenyl)-4-(trifluoromethyl)benzamide as Compound A and mancozeb as Compound B, separately and combined in various ratios, with doses of A, expressed as mg/l, on the abscissa and doses of B, expressed as mg/l, on the ordinate.
Figure 2:
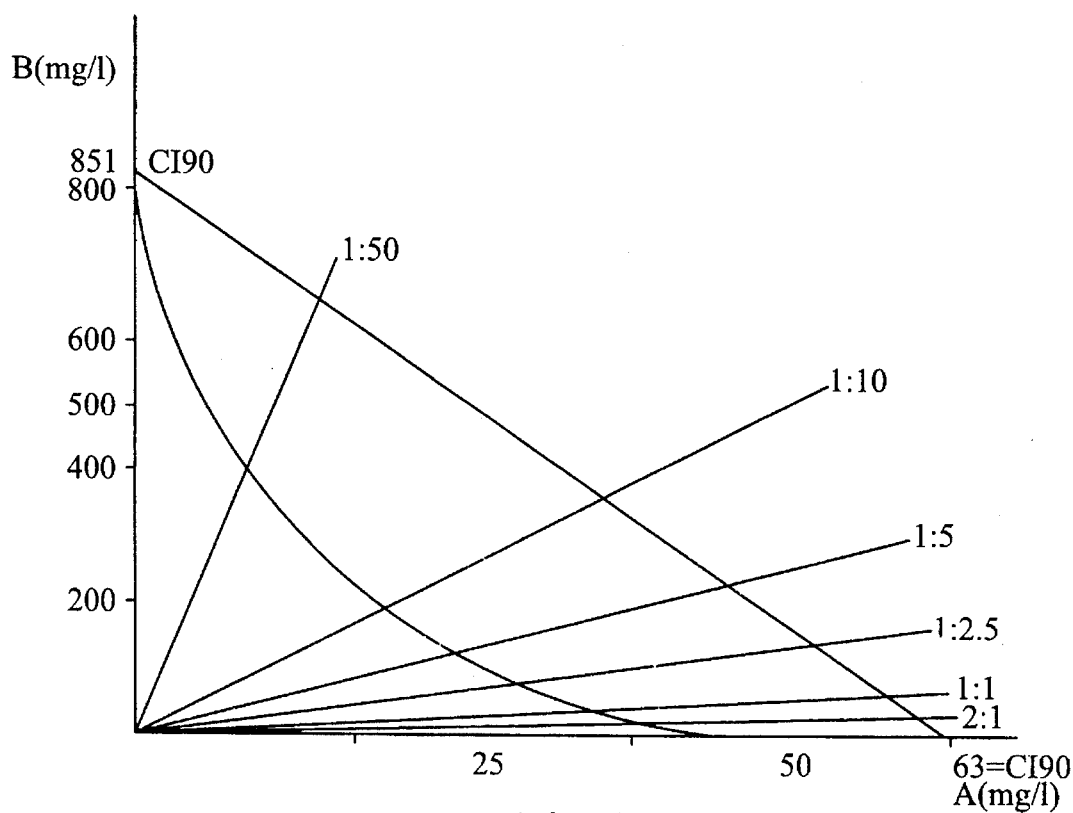
FIG. 2 is a Tammes isobole diagram based on tests conducted as described with reference to FIG. 1, except that maneb is used as Compound B.
Figure 3:
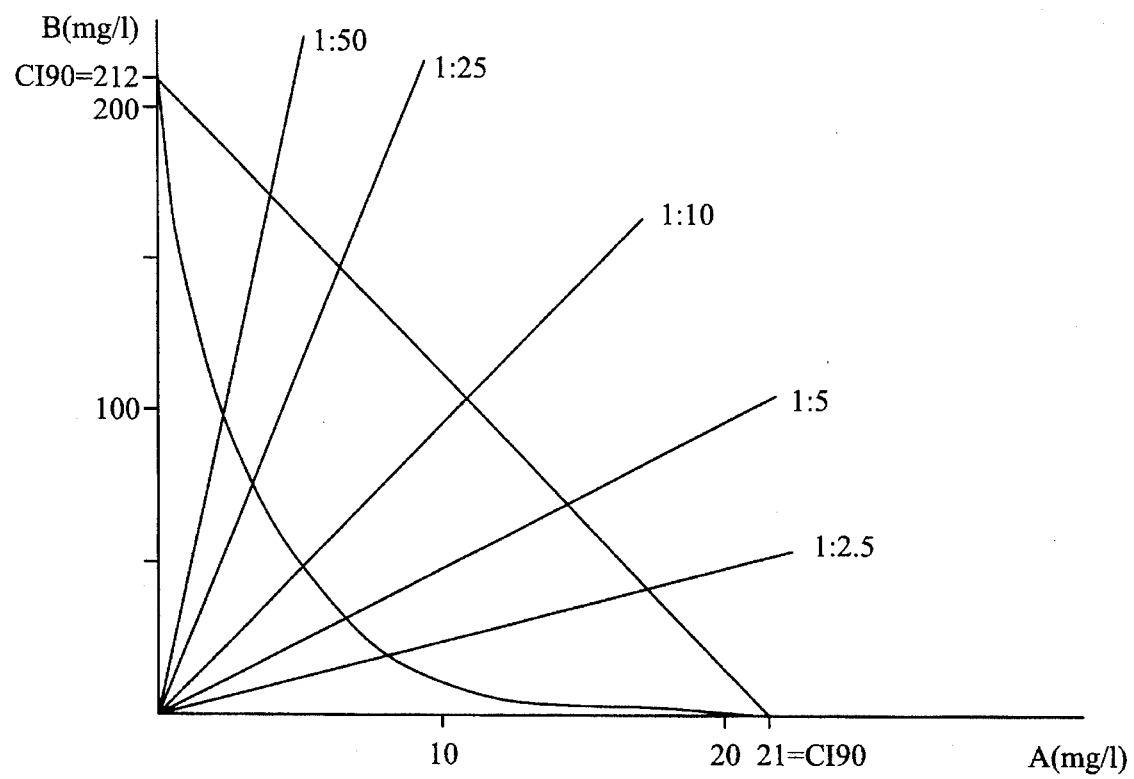
FIG. 3 is a Tammes isobole diagram based on tests of tomato seedlings infected with *Phytophthora infestans* after treatment with N-methyl-N-ethyl-2-(3,4-dimethoxyphenyl)-4-(trifluoromethyl)benzamide as Compound A and chlorothalonil as Compound B, separately and combined in various ratios, with doses of A, expressed in mg/l, on the abscissa and doses of B, expressed as mg/l, on the ordinate.

In all of the FIGURES, the abbreviation "CI90" represents the concentration giving 90% inhibition.

DETAILED DESCRIPTION OF THE INVENTION

Derivatives of formula A are preferably selected in which each of $R_1$ and $R_2$ is a hydrogen atom or a trifluoromethyl radical and each of $R_3$ and $R_4$ is a methyl or an ethyl radical.

In a particularly preferred embodiment of the invention, Compound A is N,N-diethyl-2-(3,4-dimethoxyphenyl)-4-(trifluoromethyl)benzamide or N-methyl-N-ethyl-2-(3,4-dimethoxyphenyl)-4-(trifluoromethyl)benzamide.

"An acylalanine" as used herein is preferably understood to mean a compound such as metalaxyl [methyl N-(2,6-dimethylphenyl)-N(methoxyacetyl)alaninate], benalaxyl [methyl N-(2,6-dimethylphenyl-N-(phenylacetyl)alaninate] to or furalaxyl, oxadixyl [N-(2,6-dimethylphenyl)-2-methoxy-N-(2-oxo-3-oxazolidinyl)acetamide] and the acylamide ofurace [2-chloro-N-(2,6-dimethylphenyl)-N-(tetrahydro-2-oxo-3-furanyl)acetamide].

"An acetamide" as used herein is preferably understood to mean a compound such as cymoxanil, i.e. 2-cyano-N-[(ethylamino)carbonyl]-2-(methoxyimino)acetamide.

"A copper derivative" as used herein is preferably understood to mean a derivative such as copper sulfate neutralized with lime or Bordeaux mixture, cuprous oxide or copper oxychloride.

"A methoxyiminoacetate" as used herein is preferably understood to mean, in particular, methyl-(E)-methoxyimino[α-(tolyloxy)-o-tolyl]acetate.

According to the present invention, the constituents of the combination are in an amount such that their ratio by weight A/B is between about 0.001 and about 100/1. More particularly, Compounds A and B are present in the combination in a synergistic fungicidally effective amount.

In an entirely unexpected way, the combination of the present invention significantly improves the action of the active materials taken separately for a certain number of fungi which are particularly harmful to crops such as, in particular, the vine, the solanaceae and vegetable crops. This improvement is reflected by an extension in the spectrum of diseases which can be controlled, an increase in the persistence of the protection with respect to known active materials and a decrease in the doses of each of the constituents, which is particularly advantageous for the user and the environment.

"Combination" of Compounds A and B is understood to mean any combination of the two compounds, it being possible for the latter to be applied simultaneously, advantageously as a tank-mix or as a ready-mix, or successively but sufficiently close together for the actions to be able to be combined.

The instant combination exhibits synergistic properties proved by the application of the method of Tammes, "Isoboles, a graphic representation of synergism in pesticides", *Netherlands Journal of Plant Pathology*, 70(1964), pp. 73–80 or as defined by L. E. Limpel, P. H. Schuldt and D. Lammont, 1962, Proc. NEWCC, 16:48–53, by using the formula:

$$E = X + Y - \frac{XY}{100}$$

wherein:

E is the expected percentage of inhibition of growth of the fungus by a mixture of the two fungicities A and B at defined doses;

X is the observed expected percentage of inhibition by the fungicide A at a defined dose; and Y is the observed expected percentage of inhibition by the fungicide B at a defined dose.

When the observed percentage of inhibition of the combination is greater than E, synergy exists.

According to the present invention, the constituents of the combination are in an amount such that their ratio by weight A/B is be about 0.001 and about 100/1 and preferably between about 0.001 and about 5/1.

Preferably, when B is maneb or mancozeb, the A/B ratio is between about 0.05 and about 5/1, more preferably between about 0.1 and about 4/1.

Preferably, when B is folpet, the A/B ratio is between about 0.05 and about 5/1, more preferably between about 0.1 and about 4/1.

Preferably, when B is a copper derivative, the A/B ratio is between about 0.01 and about 5/1, more preferably between about 0.1 and about 4/1.

Preferably, when B is phosethyl-Al or phosphorous acid or one of its salts, the A/B ratio is between about 0.001 and about 5/1, more preferably between about 0.1 and about 4/1.

Preferably, when B is chlorothalonil, the A/B ratio is between about 0.01 and about 1, more preferably between about 0.02 and about 0.4/1.

Preferably, when B is an acylalanine, the A/B ratio is between about 0.05 and about 5/1, more preferably between about 0.1 and about 4/1.

Preferably, when B is fluazinam, the A/B ratio is between about 0.05 and about 5/1, more preferably between about 0.1 and about 4/1.

Preferably, when B is an acetamide, the A/B ratio is between about 0.05 and about 5/1, more preferably between about 0.1 and about 4/1.

Preferably, when B is a methoxyacrylate or methoxyiminoacetate, the A/B ratio is between about 0.01 and about 5/1, more preferably between about 0.1 and about 4/1.

The following Examples illustrate the remarkable properties of the combinations according to the invention.

EXAMPLE 1

In vivo preventive test on *Plasmopara viticola*

Vine (*Vitis vinifera*) cuttings, variety Chardonnay, are grown in small pots. When these plants are 2 months old (8- to 10-leaf stage, height of 10 to 15 cm), they are treated by spraying with formulated products A and B (emulsifiable concentrate, wettable powder) and by the tank-mix of these products to be tested in the case of an A+B combination for respective A/B ratios by weight indicated in the FIGURES described below.

Compound A is N-methyl-N-ethyl-2-(3,4-dimethoxyphenyl)-4-(trifluoromethyl)benzamide and Compound B is, respectively, mancozeb, maneb, folpet, phosethyl-Al, a copper derivative (oxychloride) or phosphorous acid. Seedlings, used as controls, are treated with a treatment slurry which is similar but does not contain active material ("formulation blank").

The effectiveness of the treatments is compared in the context of a preventive application 24 hours before infection of the plants or of a curative application 24 hours after infection. Infection is produced by spraying with an aqueous suspension of spores of *Plasmopara viticola*, which suspension in obtained from sprouted leaves infected 7 days previously. These spores are suspended at a concentration of 100,000 units per $cm^3$.

The infected seedlings are then incubated for two days at approximately 18° C., in an atmosphere saturated with moisture, and then for 5 days at 20–22° C. at 90–100% relative humidity.

Figure 4:
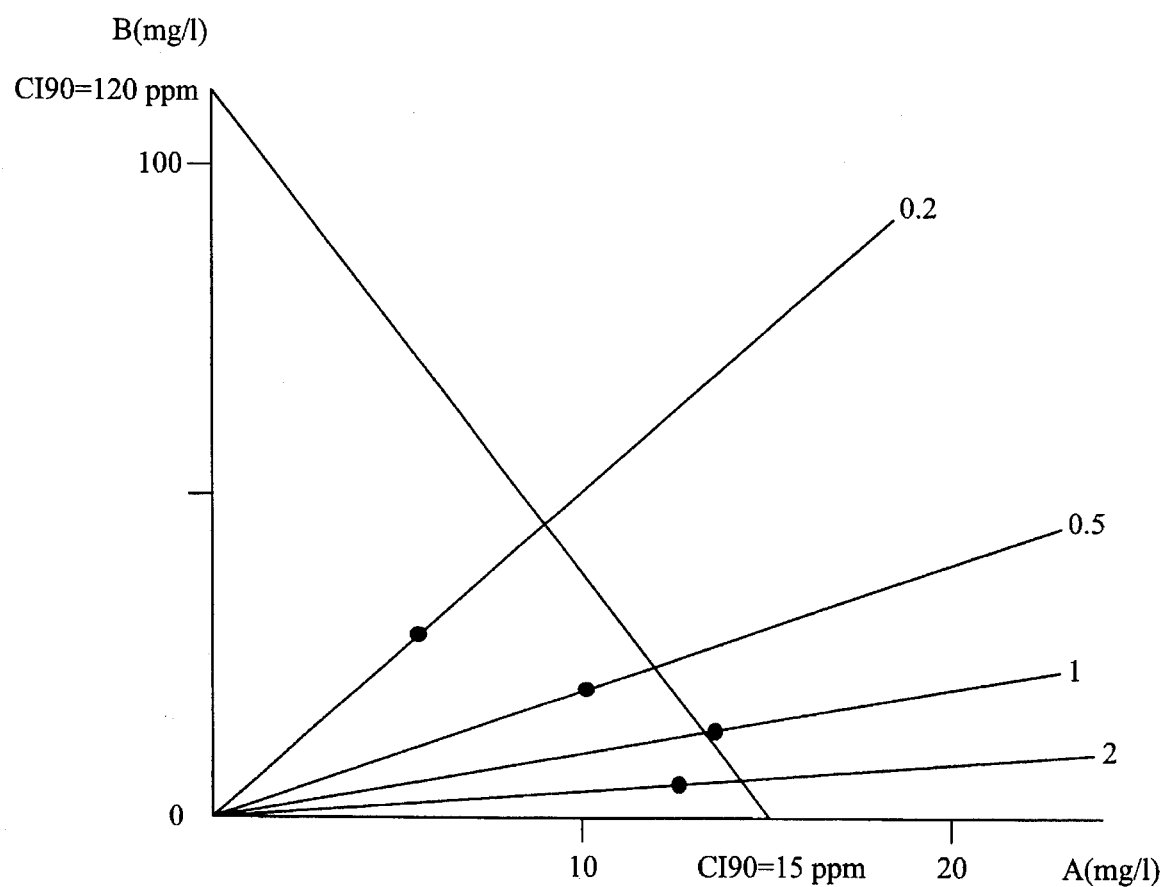
FIG. 4 is a Tamroes isobole diagram based on tests conducted as described with reference to FIG. 1, except that folpet is used as Compound B.

Reading is carried out 7 days after infection. The results obtained are shown in the form of points in a Tammes isobole diagram, with the doses of A, expressed as mg/l, on the abscissa and the doses of B, also expressed as mg/l, on the ordinate. The isoboles of:

FIG. 1 for mancozeb,

FIG. 2 for maneb,

FIG. 4 for folpet, and

Figure 5:
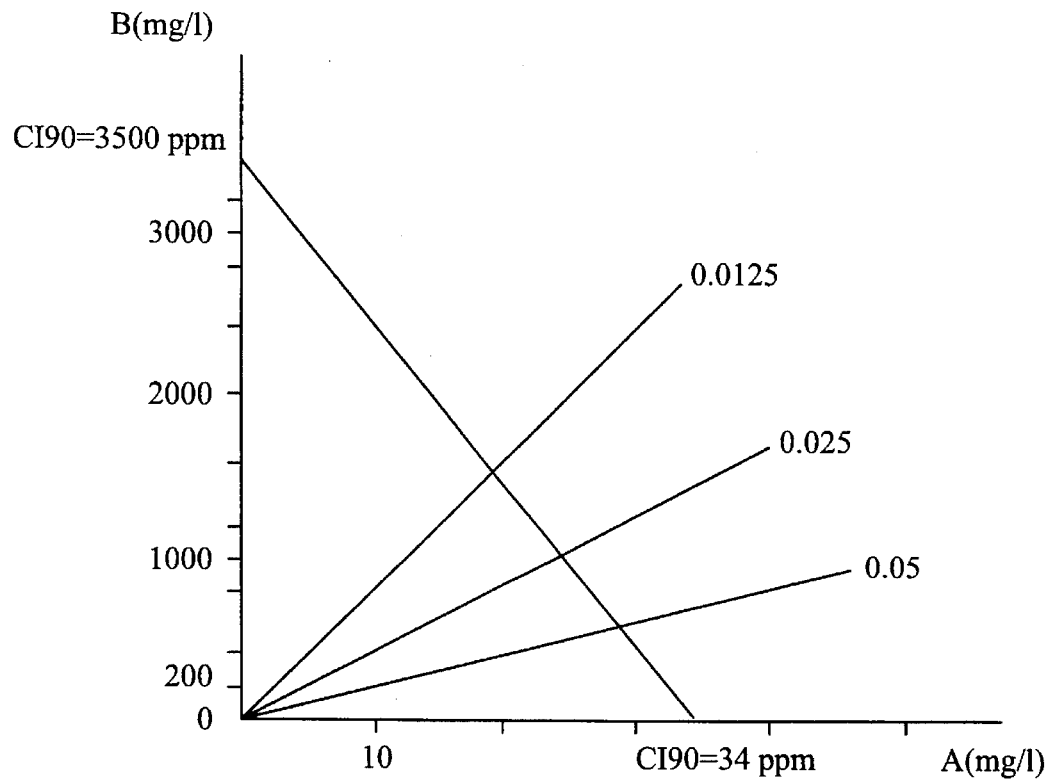
FIG. 5 is a Tammes isobole diagram based on tests conducted as described with reference to FIG. 1, except that phosphorous acid is used as Compound B.
Figure 6:
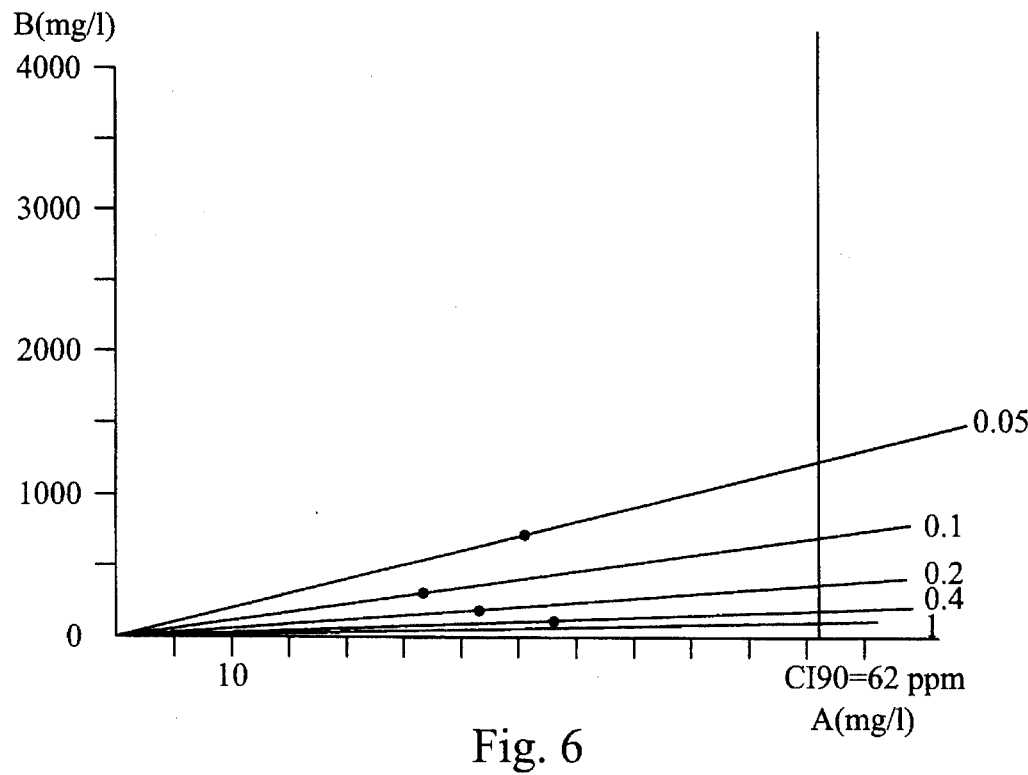
FIG. 6 is a Tamroes isobole diagram based on tests conducted as described with reference to FIG. 3, except that phosethyl-Al is used as Compound B.
Figure 7:
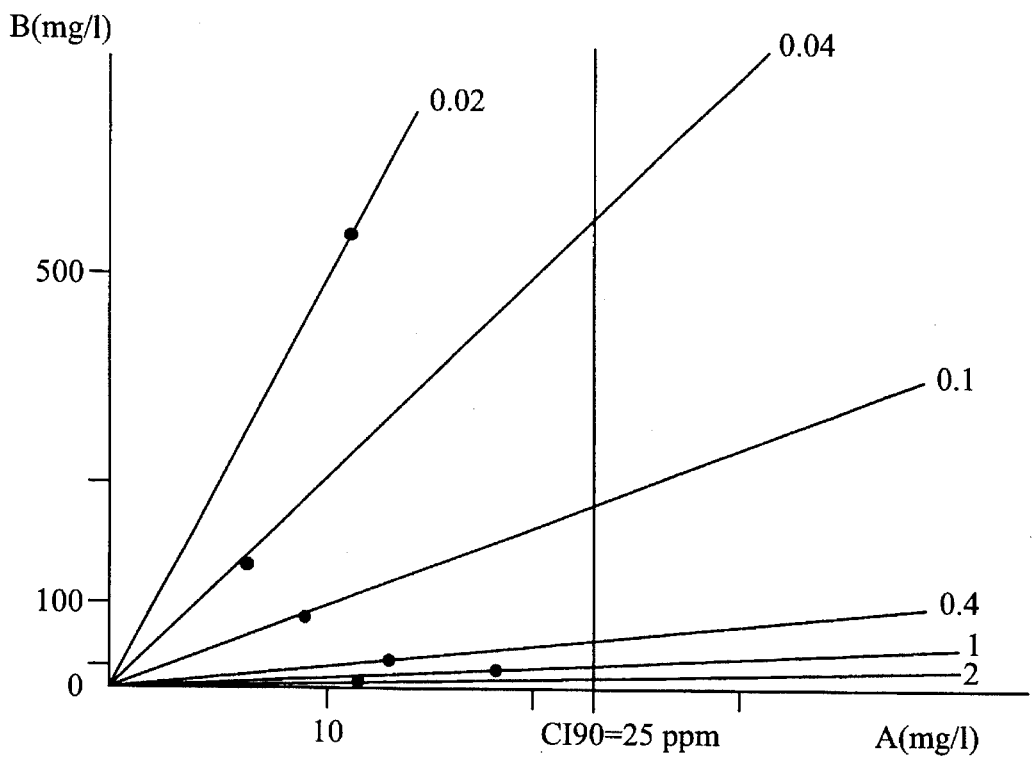
FIG. 7 is a Tammes isobole diagram based on tests conducted as described with reference to FIG. 3, except that metalaxyl is used as Compound B.
Figure 8:
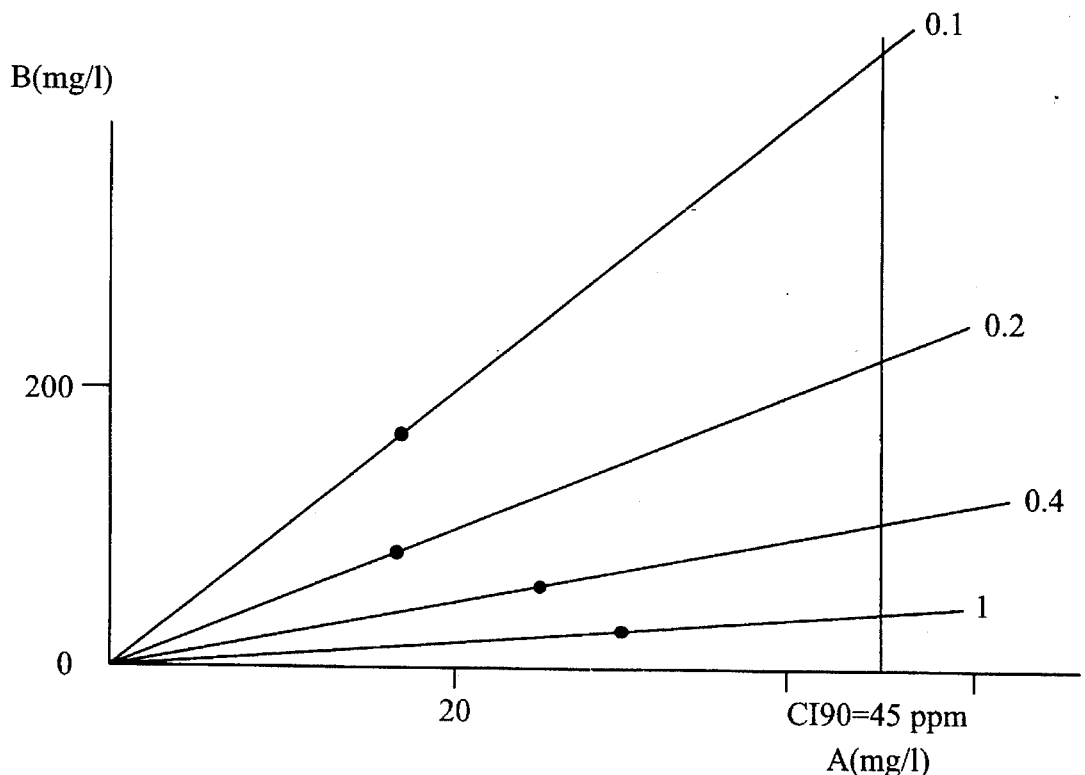
FIG. 8 is a Tammes isobole diagram based on tests conducted as described with reference to FIG. 3, except that benalaxyl is used as Compound B.
Figure 9:
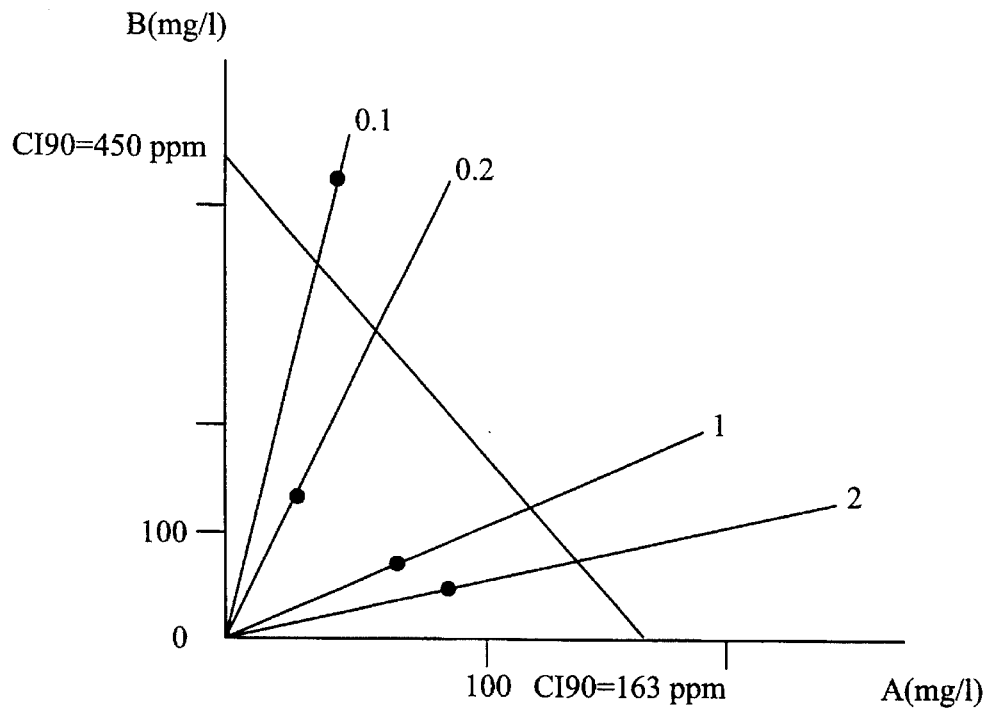
FIG. 9 is a Tammes isobole diagram based on tests conducted as described with reference to FIG. 3, except that cymoxanyl is used as Compound B.
Figure 10:
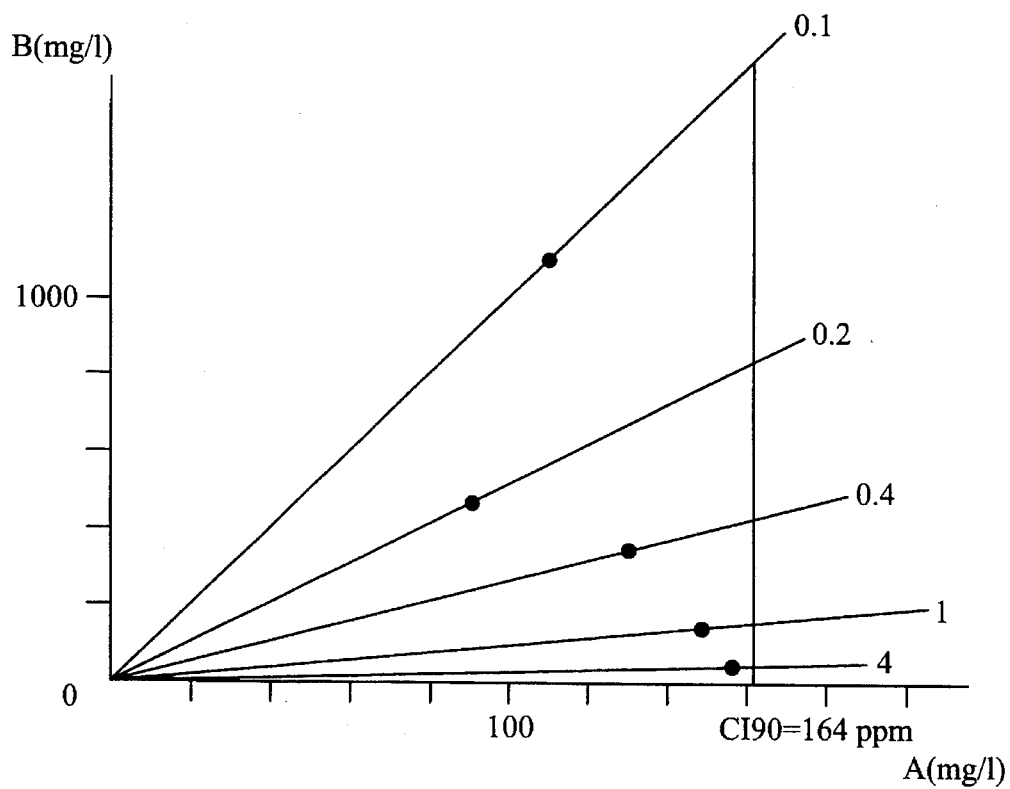
FIG. 10 is a Tammes isobole diagram based on tests conducted as described with reference to FIG. 3, except that methyl-(E)-methoxyimino[α-(tolyloxy)-o-tolyl]acetate (BASF 490F) is used as Compound B.
Figure 11:
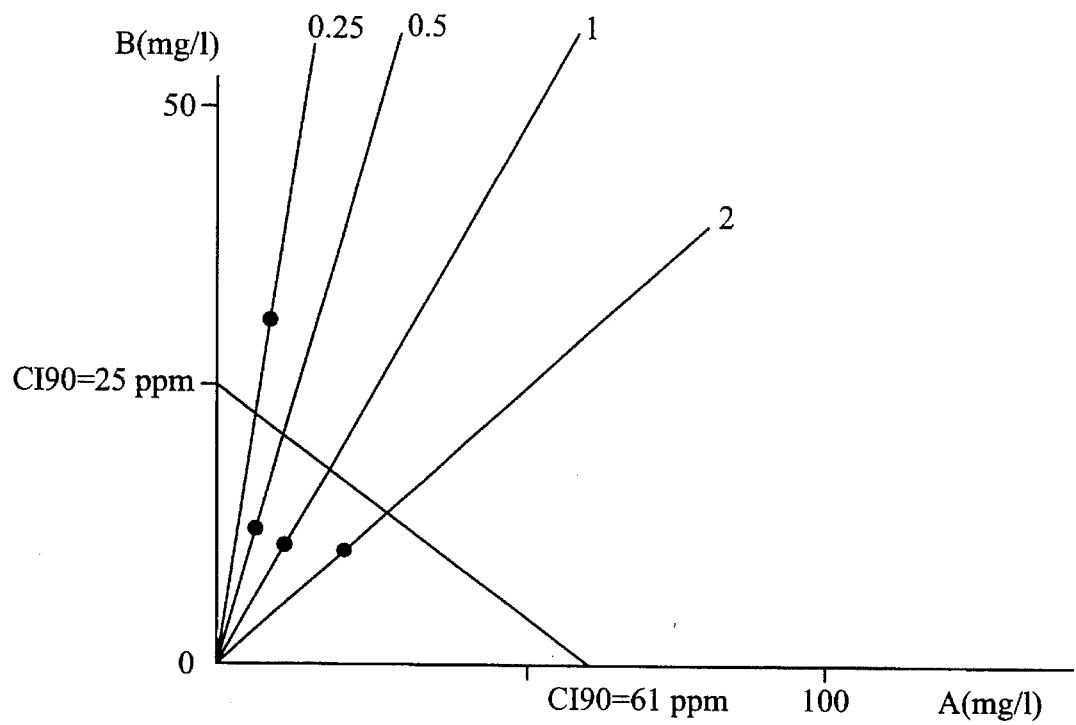
FIG. 11 is a Tammes isobole diagram based on tests of vine cuttings infected with *Plasmopara viticola* before treatment with N-methyl-N-ethyl-2-(3,4-dimethoxyphenyl)-4-(trifluoromethyl)benzamide as Compound A and oxadixyl as Compound B, separately and combined in various ratios, with dosages of A, expressed as mg/l, on the abscissa and doses of B, expressed as mg/l, on the ordinate.
Figure 12:
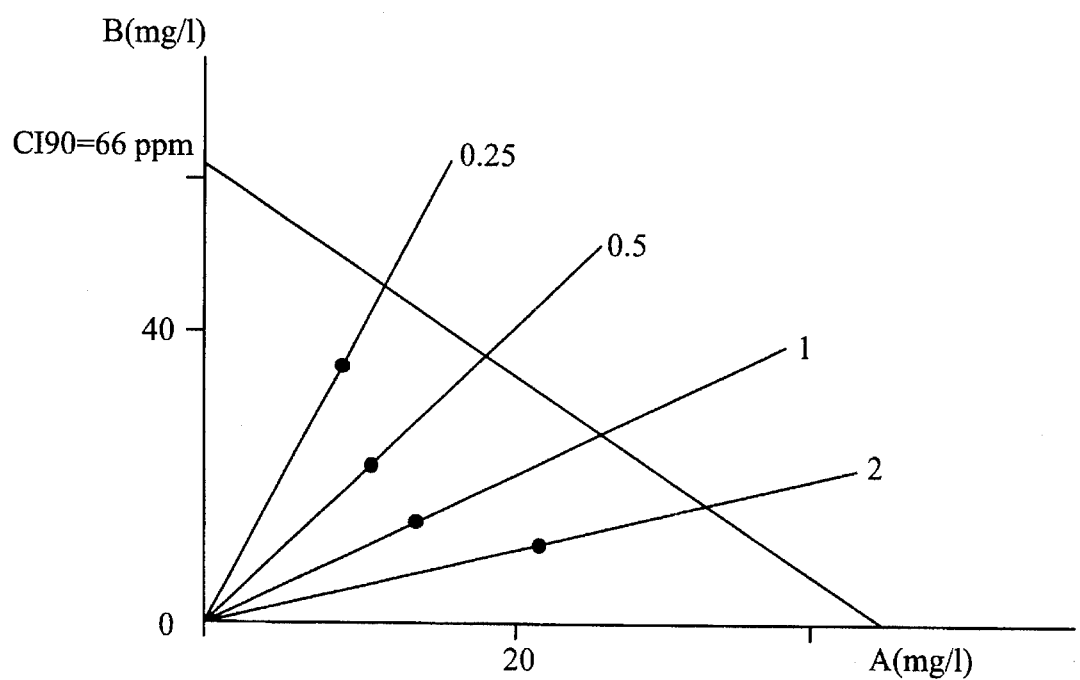
FIG. 12 is a Tammes isobole diagram based on tests conducted as described with reference to FIG. 11, except that cymoxanil is used as Compound B.

FIG. 5 for phosphorous acid, are obtained which show synergy of the corresponding combinations with Compound A. Moreover, at least additive results are obtained with combinations of Compound A with phosethyl-Al or a copper derivative such as the oxychloride.

Very similar results are obtained with N,N-diethyl-2-(3,4-dimethoxyphenyl)-4-(trifluoromethyl)benzamide used in place of the N-methyl-N-ethyl derivative as Compound A.

EXAMPLE 2

In vitro preventive test on *Phytophthora infestans* (tomato late blight)

Tomato seedlings (Marmande variety) are grown in small pots. When these seedlings are one month old (5- to 6-leaf stage, height 12 to 15 cm), they are treated by spraying with the formulated products A and B (emulsifiable concentrate, wettable powder) and by the tank-mix of these products to be tested in the case of an A+B combination for respective A/B ratios by weight indicated in the FIGURES described below. Compound A is N-methyl-N-ethyl-2-(3,4-dimethoxyphenyl)-4-(trifluoromethyl)benzamide and Compound B is, respectively, chlorothalonil, phosethyl-Al, metalaxyl, benalaxyl, cymoxanyl or methyl-(E)-methoxyimino[α-(tolyloxy)-o-tolyl]acetate.

The efficiencies of the treatments are compared after preventive application 48 hours before infection of the plants by spraying with an aqueous suspension of spores (30,000 sp/ml) of *Phytophthora infestans.*

After this infection, the tomato seedlings are incubated for 7 days at approximately 20° C. in an atmosphere saturated with moisture.

The isoboles of:

FIG. 3 for chlorothalonil,

FIG. 6 for phosethyl-Al,

FIG. 7 for metalaxyl,

FIG. 8 for benalaxyl,

FIG. 9 for cymoxanil, and

FIG. 10 for methyl-(E)-methoxyimino[α-(tolyloxy)-o-tolyl]acetate (BASF 490F), are obtained which illustrate the synergy of the corresponding combinations with Compound A. Moreover, at least additive results are obtained with combinations of the Compound A with, as Compound B, a copper derivative such as the oxychloride.

Very similar results are obtained with N,N-diethyl-2-(3,4-dimethoxyphenyl)-4-trifluoromethyl)benzamide used in place of the N-methyl-N-ethyl derivative as Compound A.

EXAMPLE 3

In vivo curative test on *Plasmopara viticola*

Vine (*Vitis vinifera*) cuttings, variety Chardonnay, are grown in small pots. When these plants are two months old (8- to 10-leaf stage, height 10 to 15 cm), they are treated by spraying with formulated products A and B (emulsifiable concentrate, wettable powder) and by the tank-mix of these products to be tested in the case of an A+B combination for respective A/B ratios by weight indicated on the FIGURES described below.

Compound A is N-methyl-N-ethyl-2-(3,4-dimethoxyphenyl)-4-(trifluoromethyl)benzamide and Compound B is, respectively, oxadixyl or cymoxanyl.

Seedlings, used as controls, are treated with a treatment slurry which is similar but does not contain active material ("formulation blank").

The effectiveness of the treatments is compared in the context of a curative application 24 hours after infection. Infection is produced by spraying with an aqueous suspension of spores of *Plasmopara viticola,* which suspension is obtained from sporulated leaves infected seven days previously. These spores are suspended at a concentration of 100,000 units per $cm^3$. The infected seedlings are then incubated for two days at approximately 18° C., in an atmosphere saturated with moisture, and then for five days at 20°–22° C. at 90–100% relative humidity.

Reading is carried out seven days after infection. The results obtained are shown in the form of points in a Tammes isobole diagram, with the doses of A, expressed as mg/l, on the abscissa and the doses of B, also as mg/l, on the ordinate. The isoboles of:

FIG. 11 for oxadixyl, and

FIG. 12 for cymoxanyl, are obtained which show the synergy of the corresponding combinations with Compound A.

These results clearly illustrate the remarkable synergy of the combinations according to the invention.

The combinations are advantageously applied at doses of about 0.01 to about 5 kg/ha and more specifically of about 0.02 to about 2 kg/ha approximately.

The compounds of the combinations according to the invention are rarely used alone in practice. They are most often part of compositions. These compositions, which can be used for protecting plants against fungal diseases, or in plant growth regulatory compositions, contain, as active material, a fungicidally effective amount of at least one combination (i.e. at least one Compound A and at least one Compound B) according to the invention as described above in combination with one or more agriculturally acceptable, solid or liquid, inert vehicles and/or surface-active agents which are compatible with the active material and which are also agriculturally acceptable. In particular, the inert and conventional vehicles and the conventional surface-active agents can be used.

In the present account, the term "vehicle" denotes a natural or synthetic, organic or inorganic material with which the active material is combined to facilitate its application on the plant, on seeds or on the ground. This vehicle is thus generally inert and it must be agriculturally acceptable, especially on the treated plant. The vehicle can be solid (clays, natural or synthetic silicates, silica, resins, waxes, solid fertilizers and the like), liquid (water, alcohols, ketones, petroleum fractions, aromatic or paraffinic hydrocarbons, or chlorinated hydrocarbons) or a gas.

The surface-active agent can be an emulsifying, dispersing or wetting agent of ionic or nonionic type. There may be mentioned, for example, salts of polyacrylic acids, salts of lignosulfonic acids, salts of phenolsulfonic or naphthalenesulfonic acids, polycondensates of ethylene oxide with fatty alcohols or with fatty acids or with fatty amines, substituted phenols (especially alkylphenols or arylphenols), salts of esters of sulfosuccinic acids, taurine derivatives (especially alkyltaurates) or phosphoric esters of polyoxyethylenated phenols or alcohols. The presence of at least one surface-active agent is generally indispensable when the active material and/or the inert vehicle are not soluble in water and when the carrier agent of the application is water.

The compositions used in the invention can be in fairly diverse, solid, liquid or fluid, forms.

There may be mentioned, as forms of fluid compositions, or liquids, especially emulsifiable concentrates, emulsions, aqueous suspension concentrates, pastes, solutions, in particular water-soluble concentrates or concentrated solutions in an organic medium (ULV solution), and aerosols.

The emulsifiable or soluble concentrates most often comprise from about 10 to about 80% of active material, while emulsions or solutions ready for application generally contain from about 0.001 to about 20% of active material. In addition to the active material and the solvent, the emulsifiable concentrates can contain, when this is necessary, a suitable cosolvent and from about 2 to about 20% of suitable additives, such as stabilizing agents, penetrating agents, corrosion inhibitors, dyes or adhesives.

From these concentrates, it is possible to obtain, by dilution with water, emulsions of any desired concentration, which are particularly suitable for application to crops.

In all of the following Examples of compositions of the invention, the active material is a combination of the compounds of formula (A) and Compound (B) as generally defined hereinabove.

The compositions of some emulsifiable concentrates are given here as examples:

EC Example 1

| | |
|---|---|
| active material | 250 g/l |
| epoxidized vegetable oil | 25 g/l |
| mixture of alkylaryl sulfonate and ether of polyglycol and fatty alcohols | 100 g/l |
| dimethylformamide | 50 g/l |
| xylene | 575 g/l |

EC Example 2

| | |
|---|---|
| active material | 400 g/l |
| alkali metal dodecylbenzenesulfonate | 24 g/l |
| oxyethylenated nonylphenol, containing 10 molecules of ethylene oxide | 16 g/l |
| cyclohexanone | 200 g/l |
| aromatic solvent | q.s. for 1 liter |

From these concentrates, it is possible to obtain, by dilution with water, emulsions of any desired concentration, which are particularly suitable for application to leaves.

The suspension concentrates, also applicable by spraying, are prepared so as to obtain a stable fluid product which does not settle out and they generally contain from about 10 to about 75 % of active material, from about 0.5 to about 5% of surface-active agents, from about 0.1 to about 10% of thixotropic agents and from about 0 to about 10% of suitable additives, such as antifoaming agents, corrosion inhibitors, stabilizing agents, penetrating agents and adhesives and, as vehicle, water or an organic liquid in which the active material is insoluble or nearly insoluble. Certain organic solid materials or inorganic salts can be dissolved in the vehicle to aid in preventing sedimentation or as antifreezes for water.

The compositions of a number of aqueous suspension concentrates according to the invention are given here as examples:

ASC Example 1

| An aqueous suspension is prepared comprising: | |
|---|---|
| active material | 100 g/l |
| wetting agent (polyethoxylated alkylphenol) | 5 g/l |
| dispersing agent (Na naphthalenesulfonate) | 10 g/l |
| antifreeze (propylene glycol) | 100 g/l |
| thickening agent (polysaccharide) | 3 g/l |
| biocide (formaldehyde) | 1 g/l |
| water | q.s. for 1 liter |

ASC Example 2

| An aqueous suspension is prepared comprising: | |
|---|---|
| active material | 250 g/l |
| wetting agent (polyethoxylated synthetic C13 alcohol) | 10 g/l |
| dispersing agent (sodium lignosulfonate) | 15 g/l |
| antifreeze (urea) | 50 g/l |
| thickening agent (polysaccharide) | 2.5 g/l |
| biocide (formaldehyde) | 1 g/l |
| water | q.s. for 1 liter |

ASC Example 3

| An aqueous suspension is prepared comprising: | |
|---|---|
| active material | 500 g/l |
| wetting agent (polyethoxylated synthetic C13 alcohol) | 10 g/l |
| dispersing agent (salified ethoxylated polyarylphenyl phosphate) | 50 g/l |
| antifreeze (propylene glycol) | 100 g/l |
| thickening agent (polysaccharide) | 1.6 g/l |
| biocide (sodium salt of methyl 4-hydroxybenzoate) | 3.3 g/l |
| water | q.s. for 1 liter |

There may be mentioned, as solid composition forms, powders for dusting (with an active material content which can range up to about 100%) and granules, especially those obtained by extrusion, by compacting, by impregnation of a granulated vehicle, or by granulation from a powder (the content of active material in these granules being between about 0.5 and about 80% for the latter cases).

Wettable powders (or powders to be sprayed) are generally prepared so that they contain from about 10 to about 95 % of active material, and they generally contain, in addition to the solid vehicle, from about 0 to about 5% of a wetting agent, from about 3 to about 10% of a dispersing agent and, when this is necessary, from about 0 to about 10% of one or more stabilizing agents and/or other additives, such as penetrating agents, adhesives, or anticlumping agents, dyes, and the like.

The compositions by weight of a number of wettable powders are given here as examples:

WP Example 1

| | |
|---|---|
| active material | 10% |
| C13 branched-type synthetic oxo alcohol, ethoxylated with 8 to 10 molecules of ethylene oxide (wetting agent) | 0.75% |
| neutral calcium lignosulfonate (dispersing agent) | 12% |
| calcium carbonate (inert filler) | q.s. for 100% |

WP Example 2

| | |
|---|---|
| active material | 50% |
| ethoxylated fatty alcohol (wetting agent) | 2.5% |
| ethoxylated styrylphenol (dispersing agent) | 5% |
| chalk (inert vehicle) | 42.5% |

WP Example 3

| | |
|---|---|
| active material | 75% |
| wetting agent | 1.5% |
| dispersing agent | 8% |
| calcium carbonate (inert filler) | q.s. for 100% |

WP Example 4

| | |
|---|---|
| active material | 90% |
| ethoxylated fatty alcohol (wetting agent) | 4% |
| ethoxylated styrylphenol (dispersing agent) | 6% |

To obtain these powders to be sprayed or wettable powders, the active material is intimately mixed, in suitable mixers, with the additional substances and the mixture is milled with mills or other suitable grinders. Powders to be sprayed are thereby obtained with advantageous wettability and suspensibility; they can be suspensed in water at any desired concentration and this suspension can be used very advantageously in particular for application to plant leaves.

The combination according to the invention can also be used in the form of powders for dusting; it is also possible to use a composition comprising 50 g of active material and 950 g of talc; it is also possible to use a composition comprising 20 g of active material, 10 g of finely divided silica and 970 g of talc; these constituents are mixed and milled and the mixture is applied by dusting.

The granules for dusting have sizes of between about 0.1 and about 2 mm and can be manufactured by agglomeration or impregnation. In general, the granules contain from about 0.5 to about 25% of active material and from about 0 to about 10% of additives such as stabilizing agents, modifying agents for slow release, binders and solvents.

Two granule composition examples are now given:

Example 1 and G Example 2

| | | |
|---|---|---|
| active material | 50 g | 200 g |
| propylene glycol | 50 g | 50 g |
| polyglycol cetyl ether | 2.5 g | 2.5 g |
| polyethylene glycol | 35 g | 35 g |
| kaolin (particle size: from about 0.3 to about 0.8 mm) | 910 g | 760 g |

The combinations according to the invention can advantageously be formulated in the form of water-dispersible granules, which also come within the scope of the invention.

These dispersible granules, with a bulk density generally of between approximately 0.3 and approximately 0.6, have a particle size generally of between approximately 150 and approximately 2000 microns, preferably between about 300 and about 1500 microns.

The active material content of these granules is generally between approximately 1% and approximately 90%, preferably between about 25% and about 90%.

The rest of the granule is essentially composed of a solid filler and, optionally, of surface-active adjuvants which confer water-dispersibility properties on the granule. These granules can be essentially of two distinct types according to whether the filler is soluble or insoluble in water. When the filler is water-soluble, it can be inorganic or, preferably, organic. Excellent results have been obtained with urea. In the case of an insoluble filler, the latter is preferably inorganic, such as, for example, kaolin or bentonite. It is then accompanied by surface-active agents (in a proportion of from about 2 to about 20% by weight of the granule) of which more than half consists of at least one essentially anionic dispersing agent such as an alkali metal or alkaline-earth metal polynaphthalenesulfonate or an alkali metal or alkaline-earth metal lignosulfonate, the remainder consisting of nonionic or anionic wetting agents such as an alkali metal or alkaline-earth metal alkylnaphthalenesulfonate.

Moreover, although this is not indispensable, it is possible to add other adjuvants such as antifoaming agents.

The granule according to the invention can be prepared by mixing the necessary ingredients and then granulating according to several techniques known per se (granulator, fluid bed, sprayer, extrusion and the like). The preparation generally finishes with a crushing followed by a sieving to the particle size chosen within the limits mentioned above. It is preferably obtained by extrusion.

The following dispersible granule compositions are prepared by carrying out the preparation as indicated in the examples below.

DG Example 1

90% by weight of active material and 10% by weight of urea in the form of pearls are mixed in a mixer. The mixture is then milled in a pin mill. A moist powder is obtained which is extruded in a perforated-roller extruder. A granule is obtained which is dried, and then crushed and sieved, so as to keep only the granules with a size of between about 150 and about 2000 microns.

DG Example 2

The following constituents are mixed in a mixer:

| | |
|---|---|
| active material | 75% |
| wetting agent (sodium alkylnaphthalenesulfonate) | 2% |
| dispersing agent (sodium polynaphthalenesulfonate) | 8% |
| water-insoluble inert filler (kaolin) | 15% |

DG Example 3

| | |
|---|---|
| active material | 20% |
| sodium alkylnaphthalenesulfonate | 2% |
| sodium methylenebis(naphthalenesulfonate) | 8% |
| kaolin | 70% |

This mixture is granulated on a fluid bed in the presence of water and then dried, crushed and sieved so as to obtain granules with a size of between about 0.16 and about 0.40 mm.

These granules can be used alone or in solution or dispersion in water so as to obtain the required dose. They can also be used to prepare combinations with other active materials, especially fungicides, the latter being in the form of wettable powders or of granules or aqueous suspensions.

The combinations according to the invention can alternatively be formulated in the form of organic solutions which can be encapsulated, especially by interfacial polymerization, in capsules having polymeric walls, for example based on polyamides, polyureas or polyamideureas. These capsules are in the form of a concentrated aqueous dispersion which can be diluted at the time of use in order to obtain a spray slurry.

As has already been said, aqueous dispersions and emulsions, for example compositions obtained by diluting a wettable powder or an emulsifiable concentrate according to the invention with water, come within the general scope of the compositions which can be used in the present invention. Emulsions can be of the water-in-oil or oil-in-water type and they can have a thick consistency, like that of a "mayonnaise".

The invention furthermore relates to a method for the treatment, both curative and preventive, of plants against diseases caused by phytopathogenic fungi, especially those of the family of the Oomyceteae of the type Phytophthora sp., for example *Phytophthora infestans* (potato blight or tomato late blight), *Phytophthora citrophthora, Phytophthora capsici, Phytophthora cactorum, Phytophthora palmivora, Phytophthora cinnamomi, Phytophthora megasperma* or *Phytophthora parasitica*, Peronospora sp. (especially tobacco downy mildew), Plasmopara sp., especially *Plasmopara viticola* (grape downy mildew) and *Plasmopara halstedei* (sunflower downy mildew), Pseudoperonospora sp. (especially downy mildew of cucurbitaceous plants and hop downy mildew) or *Bremia lactucae* (lettuce downy mildew), and soil fungi, this method comprising applying a combination according to the invention. The excellent curative activity of the combinations according to the invention is particularly advantageous since it makes it possible to reduce the number of systematic preventive treatments while ensuring good control of the parasites.

This process is characterized in that it consists in applying, to these plants or to the locus in which they grow, an effective amount of a combination according to the invention, preferably of a composition containing a combination according to the invention as active material. "Effective amount" is understood to mean an amount sufficient to make possible control and destruction of the fungus present on these plants, i.e. a fungicidally effective amount. The use doses can, however, vary within wide limits depending on the fungi to be controlled, the type of crop, the climatic conditions and the combination used.

In practice, doses ranging from about 1 g/hl to about 500 g/hl, corresponding substantially to doses of active material per hectare of from about 10 g/ha to about 5000 g/ha approximately, generally give good results.

There may be mentioned, as examples of treatment processes which can be used, leaf or soil spraying, dusting, steeping, incorporation in the soil of granules, powders or slurries, sprinkling, injection into trees, painting and seed treatment. The instant combination of Compounds A and B can be applied simultaneously or successively. When applied successively, the Compounds A and B must be applied sufficiently close together that they exert an effective combined action.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely to the scope of the following claims, including equivalents thereof.

What is claimed is:

1. A fungicidal combination comprising:
   (a) a Compound A which is N-methyl-N-ethyl-2-(3,4-dimethoxyphenyl)-4-(trifluoromethyl)benzamide; and
   (b) a Compound B which is maneb or mancozeb;
   the components A and B of the combination being present in a synergistic fungicidally effective amount, the A/B ratio by weight being between about 0.001 and about 100/1.

2. The fungicidal combination according to claim 1, wherein the A/B ratio by weight is between about 0.001 and about 5/1.

3. The fungicidal combination according to claim 2, wherein the A/B ratio by weight is between about 0.05 and about 5/1.

4. The fungicidal combination according to claim 3, wherein the A/B ratio by weight is between about 0.1 and about 4/1.

5. A fungicidal composition comprising:
   (i) a fungicidally effective amount of a combination comprising:
      (a) a Compound A which is N-methyl-N-ethyl-2-(3,4-dimethoxyphenyl)-4-(trifluoromethyl)bennnzamide; and
      (b) a Compound B which is maneb or mancozeb;
      the components A and B of the combination being present in a synergistic fungicidally effective amount, the A/B ratio by weight being between about 0.001 and about 100/1; and
   (ii) at least one member selected from the group consisting of an agriculturally acceptable inert vehicle and an agriculturally acceptable surface-active agent.

6. The fungicidal composition according to claim 5, wherein the A/B ratio by weight is between about 0.001 and about 5/1.

7. A method for protecting plants against fungal disease, said method comprising applying to said plants or to the locus in which they grow, in combination, a fungicidally effective amount of:
   (a) a Compound A which is N-methyl-N-ethyl-2-(3,4-dimethoxyphenyl)-4-(trifluoromethyl)benzamide; and
   (b) a Compound B which is maneb or mancozeb;
   components A and B being applied in a synergistic fungicidally effective ratio by weight of A/B of between about 0.001 and about 100/1.

8. The method according to claim 7, wherein Compounds A and B are applied simultaneously.

9. The method according to claim 8, wherein Compounds A and B are applied in a preformed combination.

10. The method according to claim 7, wherein Compounds A and B are applied successively.

11. The method according to claim 7, wherein Compounds A and B are applied preventatively.

12. The method according to claim 7, wherein Compounds A and B are applied curatively.

13. A method for protecting plants against fungal disease, said method comprising applying to said plants or to the locus in which they grow a fungicidally effective amount of a composition as claimed in claim 5.

14. A fungicidal combination comprising:
   (a) a Compound A which is N-methyl-N-ethyl-2-(3,4-dimethoxyphenyl)-4-(trifluoromethyl)benzamide; and
   (b) a Compound B which is maneb or mancozeb;
   the components A and B of the combination being present in a synergistic fungcidally effective amount wherein the A/B ratio by weight is between about 0.02 and about 2/1.

15. A fungicidal composition comprising:
   (i) a fungicidally effective amount of a combination comprising:
      (a) a Compound A which is N-methyl-N-ethyl-2-(3,4-dimethoxyphenyl)-4-(trifluoromethyl)benzamide; and
      (b) a Compound B which is maneb or mancozeb;
      the components A and B of the combination being present in a synergistic fungicially effective amount wherein the A/B ratio by weight is between about 0.02 and about 2/1; and
   (ii) at least one member selected from the group consisting of an agriculturally acceptable inert vehicle and an agriculturally acceptable surface-active agent.

16. A method for protecting plants against fungal disease, said method comprising applying to said plants or to the locus in which they grow, in combination, a fungicidally effective amount of:
(a) a Compound A which is N-methyl-N-ethyl-2-(3,4-dimethoxyphenyl)-4-(trifluoromethyl)benzamide; and
(b) a Compound B which is maneb or mancozeb;

components A and B being applied in a synergistic fungicidally effective ratio by weight of A/B of between about 0.02 and about 2/1.

* * * * *